US009889394B2

(12) United States Patent
Day et al.

(10) Patent No.: US 9,889,394 B2
(45) Date of Patent: Feb. 13, 2018

(54) ULTRASONICALLY CLEANED LOW-PRESSURE FILTER

(71) Applicant: Bio-Rad Laboratories, Inc., Hercules, CA (US)

(72) Inventors: Richard Day, Cambridge (GB); Michael Burcher, Cambridge (GB); Nathan Wrench, Cambridge (GB); Marek Myszko, Cambridge (GB); Matthew Hayes, Cambridge (GB)

(73) Assignee: Bio-Rad Laboratories, Inc., Hercules, CA (US)

(*) Notice: Subject to any disclaimer, the term of this patent is extended or adjusted under 35 U.S.C. 154(b) by 187 days.

(21) Appl. No.: 14/266,389

(22) Filed: Apr. 30, 2014

(65) Prior Publication Data
US 2014/0326080 A1    Nov. 6, 2014

Related U.S. Application Data

(60) Provisional application No. 61/819,501, filed on May 3, 2013.

(51) Int. Cl.
  *G01N 1/22*  (2006.01)
  *B01D 29/62*  (2006.01)
  *G01N 1/34*  (2006.01)
  *B01D 29/72*  (2006.01)
  *G01N 1/40*  (2006.01)

(52) U.S. Cl.
  CPC .............. *B01D 29/62* (2013.01); *G01N 1/34* (2013.01); *B01D 29/72* (2013.01); *G01N 2001/4088* (2013.01)

(58) Field of Classification Search
  CPC ........... B01D 29/62; B01D 29/72; G01N 1/34
  USPC ....................................... 73/863.23; 210/791
  See application file for complete search history.

(56) References Cited

U.S. PATENT DOCUMENTS

| 5,022,899 A | 6/1991 | Hohlfeld et al. |
| 5,276,376 A | 1/1994 | Puskas |
| 5,739,724 A * | 4/1998 | Alexandre et al. ... B06B 1/0253 310/316.01 |

(Continued)

FOREIGN PATENT DOCUMENTS

| CN | 101678250 A | 3/2010 |
| CN | 201551897 U | 8/2010 |

(Continued)

OTHER PUBLICATIONS

Author: unknown, Title: Ultrasonic Liquid Filtering-Inline Filter Cleaning, Date: Apr. 2, 2012, Publisher: Active Ultrasonic, pages: p. 1—whole document, p. 2—magnified first half of document, p. 3—magnified second half of document.*

Author: unknown, Title: MMM Generator Technology, Date: Apr. 2, 2012, Publisher: Active Ultrasonic, Pages: p. 1—whole document, p. 2—magnified first half of document, p. 3—magnified second half of document.*

(Continued)

*Primary Examiner* — Manish S Shah
*Assistant Examiner* — Roger Hernandez-Prewitt
(74) *Attorney, Agent, or Firm* — Kilpatrick Townsend & Stockton LLP

(57) ABSTRACT

A filter device having a sonotrode connected to a filtration assembly. The filtration assembly has a filter body having a fluid passage. The filter body has a filter across the fluid passage. The filter assembly has a resonant frequency and the sonotrode is adapted to vibrate the filter assembly at or near the resonant frequency.

16 Claims, 2 Drawing Sheets

(56) References Cited

U.S. PATENT DOCUMENTS

| | | | | |
|---|---|---|---|---|
| 5,828,156 | A | * | 10/1998 | Roberts ............... B06B 3/00 310/317 |
| 2005/0145567 | A1 | | 7/2005 | Quintel et al. |
| 2006/0021950 | A1 | | 2/2006 | Crandall et al. |
| 2007/0039389 | A1 | | 2/2007 | Brooks et al. |
| 2010/0143879 | A1 | | 6/2010 | Curran |
| 2010/0186524 | A1 | | 7/2010 | Ariessohn et al. |
| 2011/0079553 | A1 | * | 4/2011 | Thomson et al. . B01D 39/1623 210/489 |
| 2011/0189715 | A1 | | 8/2011 | Likuski et al. |
| 2011/0278218 | A1 | | 11/2011 | Dionne et al. |
| 2012/0103074 | A1 | | 5/2012 | Likuski et al. |
| 2013/0098827 | A1 | * | 4/2013 | Curran ............... B01L 3/50255 210/407 |

FOREIGN PATENT DOCUMENTS

| | | | |
|---|---|---|---|
| EP | 1818092 A1 | | 8/2007 |
| JP | 2003190716 A2 | | 7/2003 |
| WO | WO 2011090978 A1 | * | 7/2011 ......... G01N 35/1097 |

OTHER PUBLICATIONS

International Search Report and Written Opinion dated Aug. 28, 2014, from PCT Application No. PCT/US2014/036187, 9 pages.
"Tooltec JP100 Ultrasonic Cleaning Tank—New From Chronos !," Chronos Engineering Supplies, posted Apr. 26, 2012 by Chronos, retrieved, Aug. 11, 2014, http://www.chronos.ltd.uk/engineering-tools/2012/tooltec-jp100-ultrasonic-cleaning-tank-new-from-chronos/, 3 pages.
Anonymous: "Mastersonic—wideband sonic and ultrasonic technology for cleaning, welding, liquid processing and sonochemistry", www.mastersonics.com/documents/mmm applications/liquids_processing/ultrasonic filtration/, Nov. 9, 2016, 1 page.
MPI , "Providing Challenging Ultrasonics Solutions Ultrasonic Filtering and Inline Filter Cleaning Tubular Clamp-On Multifrequency Reactors", http://mastersonics.com/documents/mmmapplications/liquids_processing/ultrasonictiltration/filtering-&-inline-filter-cleaing.pdf, Mar. 29, 2004, pp. 4-7.
EP14792054.0 , "Extended European Search Report", dated Nov. 17, 2016, 13 pages, Author: Joris Van Lith.
CN201480024994.9, "Chinese Office Action with English Translation," dated Aug. 31, 2016, 21 pages.

* cited by examiner

ULTRASONICALLY CLEANED LOW-PRESSURE FILTER

CROSS-REFERENCES TO RELATED APPLICATIONS

This application claims the benefit of U.S. Provisional Application No. 61/819,501, filed on May 3, 2013, which is incorporated by reference herein.

BACKGROUND OF THE INVENTION

Filtering a large quantity of biological samples (e.g, several thousand) is difficult to achieve in an effective manner, especially in the case of an analytic system that prepares injection volumes for high performance liquid chromatography. In order to ensure that a sample is not dispersed in the tubing of the system, it is necessary for the internal volumes to be as small as possible. This requires the use of a filter membrane with the smallest possible cross sectional area. In the case of a diluted blood sample, the filter is required to remove a significant volume of material in the form of lipids from the walls of the blood cells, rubber cap debris, etc.

Prior filter devices using a stainless steel mesh membrane were effective, but rendered unusable after only a few uses, in some cases as little as three. Backwashing the filter can extend life (e.g., up to 30 uses), but certainly not to the degree of having a useful system. Applying ultrasonic agitation to filters has been proposed to dislodge captured particles, which can then be backwashed. However, devices for doing so require a large amount of energy and can heat the sample to such a degree that denaturing can occur. Accordingly, there remains a need to provide a repeatedly effective filtering device.

BRIEF SUMMARY OF THE INVENTION

Embodiments relate to a fluidic filter contained within a filter assembly such that fluids can be introduced on one side of the filter and removed from the other. A filter housing is in acoustic contact with a sonotrode. During a filtering operation, fluid flows through the filter that removes particulates from it. At a subsequent time during a cleaning operation, the sonotrode is excited to deliver ultrasonic energy to the filter to clean it. During the cleaning operation, there may be forward or reverse fluid flow through the filter to assist with removing the deposited particulates from the filter housing.

The combination of the filter housing and sonotrode are designed so that they have a mechanical resonant mode at an ultrasonic frequency. This corresponds to a longitudinal vibration. The electrical impedance of the sonotrode when attached to the filter housing is low when driven at this resonant frequency. This allows the sonotrode to be driven with power in excess of 1 Watt without requiring high voltage.

The filter housing and sonotrode can be attached using adhesive and/or a threaded connection.

The filter housing can be constructed from two metal parts. The filter is located between these. An over molded o-ring around the circumference of the filter material seals the filter housing and prevents fluid passing between inlet and outlet except through the filter material. Bolts around the circumference of the filter housing secure the two parts together and compress the filter seal. Alternatively, the two halves could be threaded and screwed together.

The filter housing features a shallow chamber which allows the fluid to pass over the filter material surface. Raised features above the chamber floor support the filter material, preventing it from bowing and being obstructed by contact with the chamber floor when there is a pressure differential across it.

The filter housing and sonotrode can be contained within an enclosure that is suitable for easy insertion and removal into a fluidic network. This is effected by face seals on one or two faces of the enclosure.

Some embodiments relate to a filter device having a sonotrode connected to a filtration assembly. The filtration assembly has a filter body having a fluid passage. The filter body has a filter across the fluid passage. The filter device has a resonant frequency and the sonotrode is adapted to vibrate the filter device at or near the resonant frequency.

In some embodiments, the filter body has a first filter body portion and a second filter body portion.

In some embodiments, the filter is located between the first filter body portion and the second filter body portion.

In some embodiments, the filter body defines a filter chamber within the fluid passage, the filter being positioned within the filter chamber.

In some embodiments, a portion of filter chamber defines a support feature that supports filter material of the filter.

In some embodiments, the resonant frequency is an ultrasonic frequency.

In some embodiments, the sonotrode is adapted to vibrate the filter device at the resonant frequency at a low impedance.

In some embodiments, the sonotrode is adapted to vibrate the filter device at the resonant frequency using less than 5 W of power.

In some embodiments, the filter is transverse to an axis within the sonotrode.

In some embodiments, the sonotrode is adapted to vibrate the filter device longitudinally along the axis.

Some embodiments relate to a method in which a sample is flowed through a filter device to filter the sample. Particulates are captured by a filter material of the filter assembly. The filter device is vibrated at or near a resonate frequency of the filter device to remove the particulates from the filter device. The resonant or near-resonant frequency is monitored and power input to the filter device is altered to maintain resonance or near-resonance.

In some embodiments, the removed particles are back flushed to waste.

In some embodiments, the sample comprises a blood sample.

In some embodiments, the sample is flowed from a low pressure system into the filter device.

In some embodiments, the filtered sample is flowed to an analytical section.

Some embodiments relate to a system for analyzing a sample. The system includes a low-pressure section adapted to fluidly move a sample, an analytical section adapted to analyze the sample, and a high-pressure section adapted to move the sample from the analytical section to a containment portion, such as a column or cartridge. The low-pressure section includes a filter device having a sonotrode connected to a filtration assembly. The filtration assembly has a filter body having a fluid passage. The filter body has a filter across the fluid passage. The filter assembly has a resonant frequency and the sonotrode is adapted to vibrate the filter assembly at or near the resonant frequency. A controller is coupled to the filter assembly. The controller is adapted to monitor and alter power input to the filter device to maintain resonance or near-resonance.

DETAILED DESCRIPTION OF THE INVENTION

Figure 1:
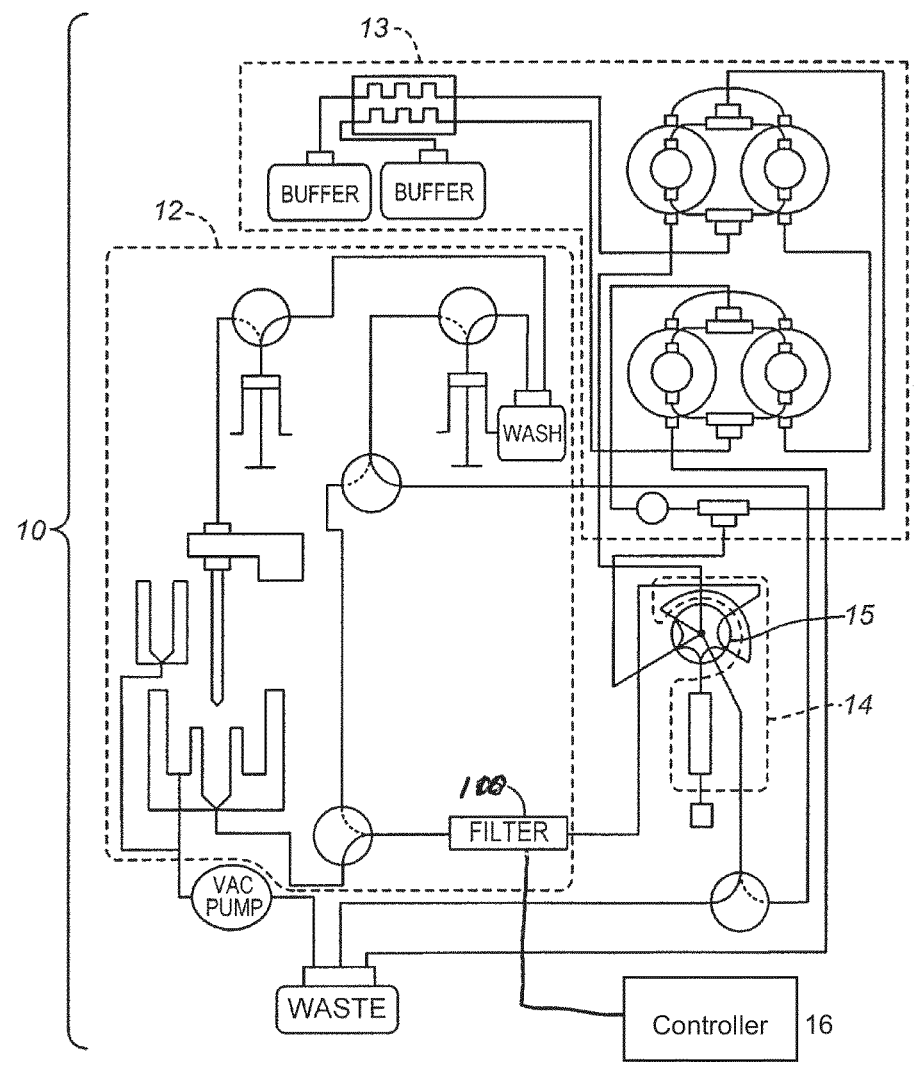
FIG. 1 shows a schematic diagram of a system for analyzing a fluid sample, according to some embodiments.

FIG. 1 is a diagram of the flow system architecture for one example of an automated blood sample analyzer 10 in accordance with some embodiments. Three sections are outlined in dashed lines: a low-pressure section 12, a high-pressure section 13, and an analytical section 14. A switching valve 15 is also shown, and a filter device 100 is shown in the low-pressure section 12. A controller 16 is connected to the filter device. The low-pressure section 12 is typically operated at pressures of 7-206 kPA, while the high-pressure section 13 is typically operated at pressures of 6,895-68,947 kPA. Similar systems are disclosed in co-assigned patent application publications US 2011/0189715 entitled "Measuring Multi-Analyte Samples using an In-Line Flow Cell" and US 2012/0103074 entitled "Automated Analyzer with Low-Pressure In-Line Filtration", both of which are incorporated by reference. It should be understood that the filter device disclosed herein can be used in such systems and low-pressure portions of similar systems.

Figure 2:
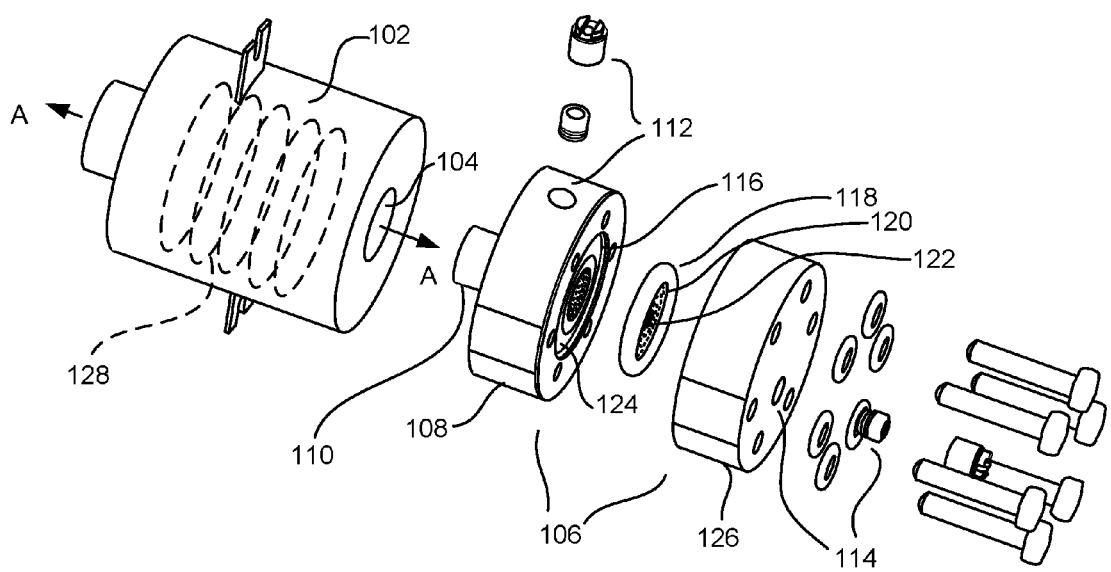
FIG. 2 shows an exploded diagram of a filter device, according to some embodiments.

FIG. 2 shows an exploded view of a filter device 100. The filter device includes a sonotrode 102, which has an elongated cylindrical body between two ends. The sonotrode includes an interface 104 at one of its ends, which here is configured as a female interface. The sonotrode houses a plurality of piezoelectric discs 128 (schematically shown with dashed lines) configured to oscillate at an ultrasonic frequency. The oscillations are transmitted along an axis A-A of the sonotrode to the interface 104.

The interface 104 of the sonotrode connects to a filter assembly 106. The filter assembly 106 is constructed from a first filter body 108 that connects to a second filter body 110. Here both bodies are cylindrical, although other shapes are possible. Generally, the filter assembly 106 may be constructed from a metal alloy (e.g., aluminum, steel, titanium). As shown, the filter bodies can mate via a plurality of bolts, although this is not critical since other types of mechanical connections are possible (e.g., interference fit, threaded).

The first filter body 108 includes an interface 110 for mating to the interface 104 of the sonotrode 102. Many types of connection configurations are possible for these interfaces, such as a threaded/bonded connection or an interference fit. The first filter body 108 also includes a first fluid port 112, which fluidly connects to an internal fluid passage.

The second filter body 126 includes a second fluid port 114 which fluidly connects to an internal passage. Both ports of the filter bodies can be used for the input or output of the filter device 100. The internal passages of the filter bodies form a singular passage when mated. Surfaces of the internal passage define a filter chamber 116 where the filter bodies meet. The filter chamber 116 houses a filter 118, which includes an outer compressible seal 120 that supports and surrounds a filter material 122. The filter 118 extends along a plane that is transverse to axis A-A.

The filter material 122 can be a membrane or mesh of metal or polymer, having a porosity that depends on the type of fluid sample to be filtered. In the case of blood samples, pores in the range of 0.1-5.0 μm can be used. The compressible seal 120 is deformed when the filter bodies are mated, thus sealing that interface. One or more support members 124 can extend from the surfaces of the filter chamber 116 that contact and support the filter material during cleaning activities.

When assembled, the filter device 100 has a resonant frequency that is determined by mass, material, and other qualities. The resonant frequency can range from 20-400 kHz. The sonotrode 102 is adapted to oscillate at a frequency that vibrates the filter device 100 at or near the resonant frequency. For the purposes of this disclosure, the terms "near-resonance", "near-resonant", and "near the resonant frequency" means that the phase difference between the applied voltage and current to the sonotrode 102 is less than 30 degrees. While at resonance, the applied voltage and current are in phase. The oscillations are transmitted longitudinally along the A-A axis. Electrical impedance of the sonotrode 102 is relatively low (e.g., 20-500 Ohms), which allows the sonotrode to be driven at power levels of 1-5 W, and at relatively low voltages (e.g., 5-50 Vrms), as compared to prior piezoelectric actuators.

In use, the filter device 100 can be implemented in the system of the blood sample analyzer 10. A sample is flowed from the low-pressure section 12 to the filter device 100, which filters the sample. In the process, the filter 118 traps particles. The filtered sample is analyzed by the analytical section 14, which can then be injected into a column by the high-pressure system 13. The filter 118 is then vibrated by the sonotrode 102, which oscillates the filter device 100 at or near its resonant frequency. Accordingly, the particles are dislodged from the filter 118 effectively, while consuming little power. The dislodged particles are then transferred to waste, and the process can be repeated. During use, the controller 16 drives and monitors the filter device 100. A feedback sensor, such as a piezoelectric sensor, is used by the controller to monitor the vibration frequency of the filter device 100. When the measured frequency alters from resonance or near-resonance, the controller 16 alters power supplied to the sonotrode 102 to maintain resonance or near-resonance, which can change due to the presence of fluid and accumulated particles.

Example

It was determined experimentally that attaching a conventional piezo-restrictive actuator to the body of a filter housing demonstrated significant promise in improving the efficacy of cleaning, in combination with back-flushing. The action of the ultrasonic vibrations appeared to loosen debris attached to the filter membrane and thus allow it to be washed off. In this manner, early prototypes demonstrated filter lifetimes in excess of 1000 tests—a significant improvement over a filter alone.

However, the power required to drive such a piezo actuator was significant—the cleaning effect was only sufficient for a life greater than 100 tests if a power of between 10 W and 50 W was applied, using driving voltages of ~190V. With these power levels, the heating effect on the apparatus was significant, raising the risk that a blood sample could be denatured by heat. It was also potentially unsafe to operate the piezo actuator at high voltage under a single-fault condition, due to the proximity of the liquid system and electrical supply.

A sonotrode based filter assembly as disclosed herein was implemented in place of the piezo actuator based filter assembly. Because the sonotrode includes a balancing mass to preserve the momentum of the vibrations, it was possible to refine the system to operate at or near resonance. An electrical control system was also implemented to monitor and adjust the sonotrode to maintain the resonant frequency, which changes due to fluid and particles within the filter assembly. It was determined that the vibrations can be maintained at maximum amplitude with power levels of <5 W using a low voltage power supply. As a result, filter lifetimes in excess of 40,000 cycles were achieved.

Although the above description contains much specificity, these should not be construed as limitations on the scope of the invention, but merely as illustrations of some embodiments. Many possible variations and modifications to the invention will be apparent to one skilled in the art upon consideration of this disclosure.

What is claimed is:

1. A method comprising:
   flowing a sample through a filter device to filter the sample, wherein particulates are captured by a filter material of a filter assembly, wherein the filter device comprises a sonotrode having a plurality of piezoelectric discs attached to the filter assembly;
   vibrating the filter device at or near a resonate frequency of the filter device to remove the particulates from the filter material, wherein the sonotrode is operated at voltages of 5-50 Vrms and at an impedance of 20 Ohms to 500 Ohms to vibrate the filter assembly; and
   vibrating the filter device with the sonotrode in excess of 40,000 cycles without replacing the filter material,
   wherein vibrating the filter device comprises monitoring the resonant or near-resonant frequency and altering power input to the filter device with a controller to monitor the number of sonotrode cycles and to maintain a phase difference between voltage applied to the sonotrode and current applied to the sonotrode of less than 30 degrees.

2. The method of claim 1, wherein the sonotrode uses less than 5 W of power.

3. The method of claim 1, wherein the removed particles are back flushed to waste.

4. The method of claim 1, wherein a filter of the filter device extends transversely across a fluid path, wherein the filter material has a porosity with pores having a size in the range of 0.1-5.0 and wherein the filter device is vibrated longitudinally along a longitudinal axis of the filter device.

5. The method of claim 1, wherein the sample comprises a blood sample.

6. The method of claim 1, wherein the sample is flowed from a low-pressure system into the filter device.

7. The method of claim 6, wherein the filtered sample is flowed to an analytical section.

8. A system for analyzing a sample, comprising:
   a low pressure section adapted to fluidly move a sample;
   an analytical section adapted to analyze the sample;
   a high-pressure section adapted to move the sample from the analytical section to a containment portion;
   wherein the low-pressure section includes a filter device comprising:
      a body comprising a sonotrode, the sonotrode having a plurality of piezoelectric discs and is operated at voltages of 5-50 Vrms;
      a filtration assembly connected to the body, the filtration assembly comprising a filter body having a fluid passage, the filter body having a filter across the fluid passage,
      wherein the filter has a porosity with pores having a size in the range of 0.1-5.0 µm, wherein the filter assembly has a resonant frequency and wherein the sonotrode is adapted to vibrate the filter assembly at or near the resonant frequency at an impedance of 20 Ohms to 500 Ohms, and further wherein the sonotrode is configured to vibrate in excess of 40,000 cycles without having to replace the filter; and
      a controller coupled to the filter assembly, the controller adapted to monitor the number of sonotrode cycles and to monitor and alter power input to the filter device to maintain resonance or near-resonance.

9. The system of claim 8, wherein the filter body comprises a first filter body portion and a second filter body portion.

10. The system of claim 9, wherein the filter is located between the first filter body portion and the second filter body portion.

11. The system of claim 8, wherein the filter body defines a filter chamber within the fluid passage, the filter being positioned within the filter chamber.

12. The system of claim 11, wherein a portion of filter chamber defines a support feature that supports filter material of the filter.

13. The system of claim 8, wherein the resonant frequency is an ultrasonic frequency.

14. The system of claim 13, wherein the sonotrode is adapted to vibrate the filter device at the resonant frequency using less than 5 W of power.

15. The system of claim 8, wherein the filter is transverse to an axis within the sonotrode.

16. The system of claim 15, wherein the sonotrode is adapted to vibrate the filter device longitudinally along the axis.

* * * * *

UNITED STATES PATENT AND TRADEMARK OFFICE
CERTIFICATE OF CORRECTION

PATENT NO. : 9,889,394 B2
APPLICATION NO. : 14/266389
DATED : February 13, 2018
INVENTOR(S) : Richard Day et al.

Page 1 of 1

It is certified that error appears in the above-identified patent and that said Letters Patent is hereby corrected as shown below:

In the Claims

Claim 4, Line 4, "range of 0.1-5.0, and wherein the filter device is vibrated" should be changed to --range of 0.1-5.0μm, and wherein the filter device is vibrated--

Signed and Sealed this
Third Day of September, 2019

Andrei Iancu
*Director of the United States Patent and Trademark Office*